United States Patent [19]

Kurtin

[11] Patent Number: 5,030,492

[45] **Date of Patent: * Jul. 9, 1991**

[54] IMAGE TRANSFER LABEL FOR SOLVENT SENSITIVE IMAGES

[76] Inventor: Stephen Kurtin, 3835 Kingswood Road, Sherman Oaks, Calif. 91403

[ * ] Notice: The portion of the term of this patent subsequent to Feb. 13, 2007 has been disclaimed.

[21] Appl. No.: 352,126

[22] Filed: May 15, 1989

Related U.S. Application Data

[63] Continuation-in-part of Ser. No. 138,348, Dec. 28, 1987, Pat. No. 4,900,597.

[51] Int. Cl.[5] ........................ A61F 13/02; E04F 15/16

[52] U.S. Cl. ........................................ 428/41; 428/46; 428/321.5; 428/402.2; 156/236

[58] Field of Search .................. 428/41, 46, 132, 146, 428/205, 247, 354, 355, 321.5, 402.2, 402.21, 402.22, 407, 488.4, 918; 355/122, 127; 156/230, 236, 241; 430/126

[56] References Cited

U.S. PATENT DOCUMENTS

| | | | |
|---|---|---|---|
| 2,603,899 | 7/1952 | Leander | 156/248 |
| 2,783,910 | 3/1957 | Johnson | 156/241 |
| 3,376,182 | 4/1968 | Borell et al. | 156/235 |
| 3,897,587 | 2/1974 | Molner | 156/241 |
| 3,950,580 | 4/1976 | Boudet | 428/41 |
| 3,973,788 | 8/1976 | Pekko et al. | 282/1 R |
| 3,974,311 | 8/1976 | Cherrin | 40/2 R |
| 4,624,875 | 11/1986 | Watanabe et al. | 428/204 |
| 4,900,597 | 2/1990 | Kurtin | 156/241 |

FOREIGN PATENT DOCUMENTS

| | | | |
|---|---|---|---|
| 94845 | 5/1982 | European Pat. Off. | 156/240 |

*Primary Examiner*—Michael W. Ball
*Assistant Examiner*—Louis Falasco
*Attorney, Agent, or Firm*—Saul Epstein

[57] ABSTRACT

A label for transferring copies of solvent sensitive images, such as those comprised of fused toner, from one surface to another. An original image is copied on to the label by wetting the image to be copied and the label with solvent (after placing the label and the image in contact). Solvation of the image causes a likeness of the image to migrate to the label. The solvent is preferably applied by breaking solvent-filled microcapsules which are in contact with the label and/or the item which bears the original image. After solvation of the image, the label, bearing a copy of the image, can be removed from the original image bearing surface and attached to a receiving surface. The invention has particular application to the addressing of envelopes for letters printed by laser printers. In this application, a copy of the address of an intended recipient of a letter can be transferred from the letter to an envelope without destroying the original address on the letter.

39 Claims, 2 Drawing Sheets

IMAGE TRANSFER LABEL FOR SOLVENT SENSITIVE IMAGES

This is a continuation-in-part of application Ser. No. 138,348, filed 12/28/87, which is now U.S. Pat. No. 4,900,597.

BACKGROUND OF THE INVENTION

Until recently, the addressing of envelopes in a business environment has created no particular difficulty. An envelope was merely placed in a typewriter and the address typed. With the advent of automatic typewriters, this procedure became even easier. After an envelope was inserted in the typewriter, the address as it appeared on the letter was "selected" and automatically typed onto the envelope. Increasingly, however, letters are being produced by laser printers coupled to computers. Unfortunately, laser printers are not well suited for printing envelopes. There is typically no bin available for envelopes so that they must be fed by hand. Also, because of the cost of laser printers, they are often shared by two or more people, resulting in wasted time and effort as the users get up from their desks to go to the printer to feed envelopes. In addition, in order for an envelope to fit into a laser printer and/or to feed properly without skewing, it should be fed lengthwise, which requires that the address information be printed in "landscape" orientation (90 degrees to the ordinary text direction). The styles available for "landscape" printing are often very limited and more often than not, the address must be printed in a style and/or size different from the accompanying letter.

Thus, addressing of envelopes has become a problem. One solution to the problem, of course, is to have an ordinary typewriter available to type addresses. This solution is not satisfactory, however, since space around secretarial desks is usually at a premium, and matching typestyles is often difficult. The cost of the extra equipment required is an additional deterrent to this solution. Feeding sheets of adhesive-backed labels through a laser printer is not a satisfactory solution either, since a single address label is too small to feed properly, and it is usually inconvenient to collect and print a number of addresses simultaneously on a sheet of labels. There is also the ever present danger that a label will become detached from its backing sheet during transit through the printer, resulting in an expensive service call to remove the label. Using adhesive-backed labels is particularly inconvenient when the printer is shared and not at the user's desk. Prior to the present invention there was not a good solution to the problem.

The invented Image Transfer Label provides a fast and convenient way to apply an address to a business envelope where the original letter is produced by a laser printer or similar printing system, such as a xerographic copier. There are other applications for the present invention, as will no doubt occur to those skilled in the art, but the invention will be described below in the context of addressing envelopes since the invention is particularly well suited for this application.

SUMMARY OF THE INVENTION

The present invention in one of its aspects involves causing a portion of the fused toner from a xerographically reproduced image on ordinary paper (a donor sheet) to transfer to the bottom surface of a transparent transfer label and then affixing the label, including the transferred image, to a different surface, such as the face of an envelope. The original image on the donor sheet is degraded little by the transfer process, and it need not be discarded.

In some embodiments, the transfer label can consist of more than one ply, the image being transferred to an underlying ply. The image is caused to transfer by placing the image receiving surface (the under side of the transfer label, whether the label consists of one or more plies) in contact with a xerographically reproduced image on a donor sheet, and causing both the image and the receiving surface to be wet by a suitable volatile solvent. The solvent is carried in microcapsules which are placed so that when they are broken by, for example, rubbing the top surface of the transfer label, the receiving surface/image interface is wet. When the image is wet, a portion of the toner dissolves off and migrates to the receiving surface. The label is then separated from the donor sheet and the solvent allowed to evaporate. The label, including the transferred portion of the image, may be affixed to, for example, an envelope to serve as an address on the envelope. The donor sheet can be retained as a file copy of the letter sent or possibly the donor sheet can be the actual letter to be sent.

A better and more detailed understanding of the invention can be had by reference to the below description of several embodiments of the invention, which description should be read in connection with the appended Figures.

DETAILED DESCRIPTION OF THE INVENTION

Figure 1:
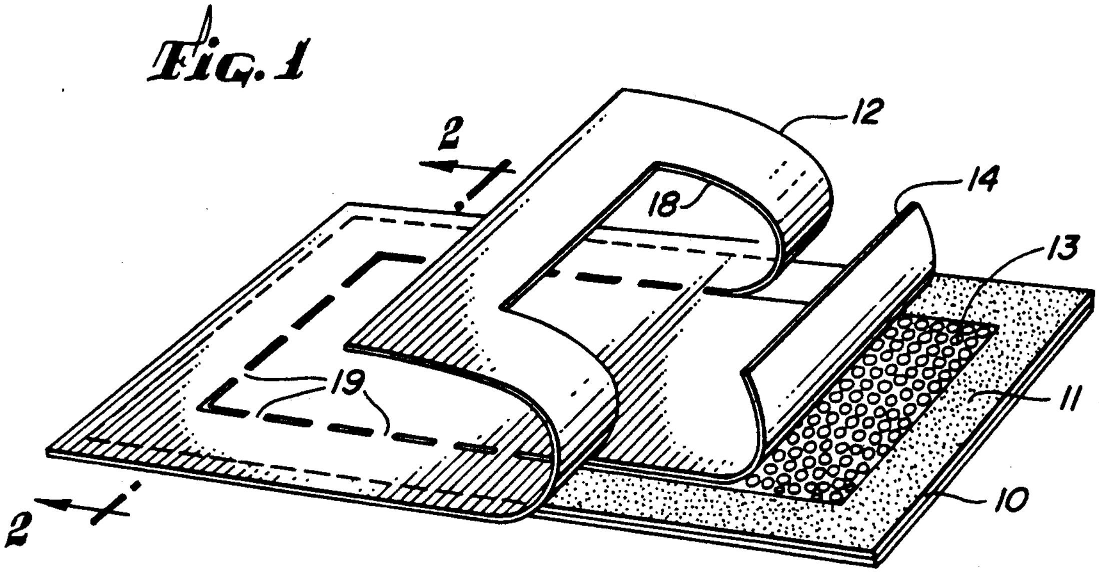
FIG. 1 is an oblique view of a first embodiment of an image transfer label according to the present invention. In order to clearly show the various parts of the label, the underside of the label is shown facing up and the protective sheets(12 and 14) are shown partially peeled off.
Figure 2:
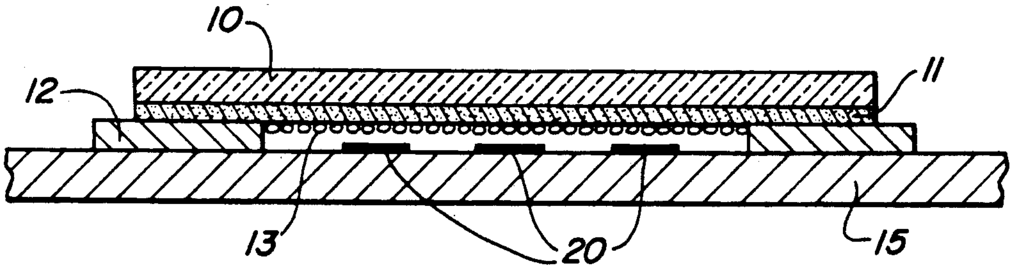
FIG. 2 is a cross sectional view of the image transfer label of FIG. 1 in place over an address on a donor sheet ready for the address to be transferred. Note that one of the protective sheets (14) has been removed. The view is taken at 2—2 of FIG. 1.

FIGS. 1 and 2 illustrate a first embodiment of an image transfer label assembly according to the present invention. A transparent label 10 is shown which has an adhesive coating 11 on one side. In this embodiment of the invention, the label 10 is the substrate to which the image is transferred. The label material is preferably a thin transparent plastic film, many suitable types of which are known to those skilled in the label art. It is preferred that the adhesive be of the self-adhesive type, but water or solvent activated adhesives could also be used. The adhesive, whether it be of the self-adhesive type or not, should be transparent.

A layer of microcapsules 13 which contain a volatile solvent covers the center portion of the label, the microcapsules being held in place by the adhesive 11. There are a number of possible formulations for the microencapsulated solvent system, the presently preferred one being 1,1,1 trichloroethane encapsulated in cellulose-based microcapsules. As will be discussed below, the size of the microcapsules is an important factor in the successful transfer of an image. Also, it may be desirable to make the adhesive underlying the microcapsules different in composition and/or thickness as compared to the adhesive around the periphery of the label. In general, better images can be transferred if the adhesive holding the microcapsules is relatively resistant to being solvated by the solvent. The optimum adhesive from an image transfer point of view may thus not be the optimum adhesive for attaching the label to the destination surface (e.g., the face of an envelope). Also, the optimum thickness of adhesive for retaining the microcapsules may not be the same as the optimum thickness for attaching the label to the destination surface.

The surface of label 10 which carries the adhesive coating and the microcapsules is covered with protective sheets (called "release liners") 12 and 14. These release liners allow the label assembly to be handled prior to use and permit the user to selectively expose the microcapsules and the adhesive as required during application. Release liner 12 is retained to the label by the adhesive coating 11 around the periphery of the label. Since the area covered by the microencapsulated solvent has no exposed adhesive, other means must be used to retain release liner 14. As shown in FIG. 1, this can be accomplished by fabricating release liners 12 and 14 from a single sheet with a discontinuous slit partially separating them. Release liner 14 is thus retained by lands 19.

To transfer an address according to the invention, a donor sheet containing the address is used. Either an original laser printed letter or a xerographically reproduced copy can be used as the donor sheet. Both are xerographic processes resulting in fused toner images. The term "xerographic" as used herein is intended to refer to any process which uses fused toner to form an image including, but not limited to, laser printers and xerographic copiers.

There may be some degradation of the address on the donor sheet on account of the transfer process and therefore it is usually preferred to use an eventual file copy of the letter as the donor. The degradation is typically minor, however, and in many cases the letter to be sent could actually be used as the donor.

In accordance with the first embodiment of the invention, the first step in the transfer process is to remove release liner 14 from the label assembly (tearing the lands 19 which hold liner 14 to liner 12). The assembly (with the microcapsules exposed) is then positioned over the address to be transferred on donor sheet 15, as shown in FIGS. 2 and 5. The dark lines 20 on sheet 15 which can be seen in FIG. 2 represent the fused toner letters on the sheet, and the dotted line 18 on FIG. 5 represents the periphery of the opening in liner 12. The top surface of label 10 is then rubbed with a finger or an instrument of some sort (while the donor sheet is supported on a hard surface such as a table) thereby breaking the microcapsules. The released solvent then wets the fused toner and some of the toner goes into solution. Since the solution is in contact with the capsule shells and the adhesive between the shells, the area of label 10 which is directly adjacent to the fused toner turns dark. The label assembly is then lifted from the donor sheet and release liner 12 removed. The label may then be positioned on a destination surface such as envelope 16, shown in FIG. 4. The exposed adhesive 11 around the periphery of the label attaches the label to the envelope, allowing the piece to be mailed. Since the label 10 is transparent, the address can easily be read. The image is also protected from damage since it is on the underside of the label.

The size of the microcapsules is critical if good results are to be obtained. If the microcapsules are too small, it can be difficult to break them using reasonable pressure. Also, an insufficient amount of solvent may be released to dissolve an adequate amount of toner. On the other hand, if the microcapsules are too large, too much solvent will be released, and smearing of the image results. The optimum size for the capsules appears to be in the about 80 to about 500 micron diameter range. Generally, in using the embodiment just described, the lower end of the range quoted produces the best results. With the embodiments described below, more solvent is needed for good results and the higher end of the range is preferred. It is also preferable in some embodiments that the capsule shells be transparent and colorless so that when in place the label will take on the color of the envelope and be unobtrusive.

Figure 3:
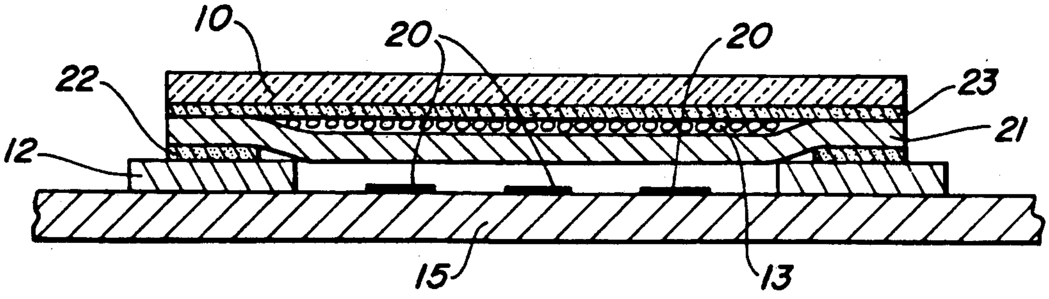
FIG. 3 is a view similar to that of FIG. 2 except that the label shown is a second embodiment of the invention.

A second embodiment of the invention is illustrated in FIG. 3. Like reference numbers refer to similar elements of the embodiment shown in FIGS. 1 and 2. In the embodiment of FIG. 3, a porous interlayer 21 is interposed between the microcapsules 13 and the donor sheet 15. A peripheral adhesive coating 22 initially retains the release liner 12 and is eventually used to affix the transfer label to its destination surface, i.e., the face of an envelope. The porous interlayer 21 may be a transparent porous plastic film or it may be any other porous material such as e.g. a thin paper sheet.

When the microcapsules are broken as by rubbing on the top surface of label 10, the released solvent flows down through the porous interlayer 21 and wets the surface of the image 20. Solvated toner then wicks up through the porous interlayer and becomes visible through the transparent label 10. Release liner 12 is then removed and the label assembly is affixed to its destination surface. Adhesive layer 22 attaches the assembly to the destination surface. If interlayer 21 is sufficiently robust, the transparent label 10 together with the microcapsule shells can be peeled off leaving the interlayer 21 only attached as the mailing label. If this alternative is utilized, there is no concern about the transparency of the microcapsule shells.

Figure 4:
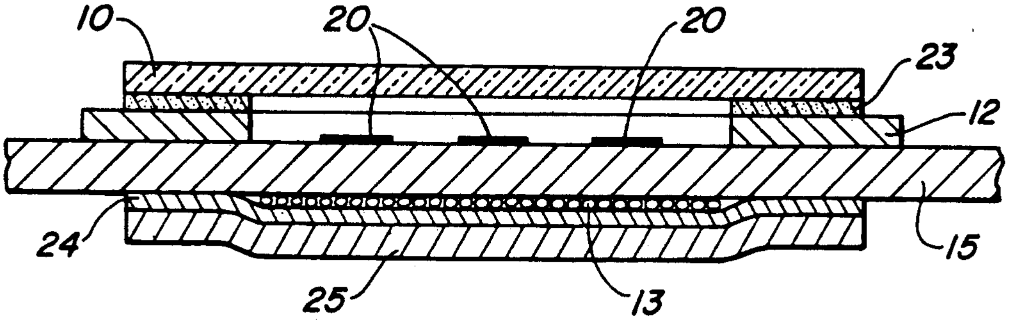
FIG. 4 is a view similar to that of FIG. 2 except that the label shown is a third embodiment of the invention.
Figure 5:
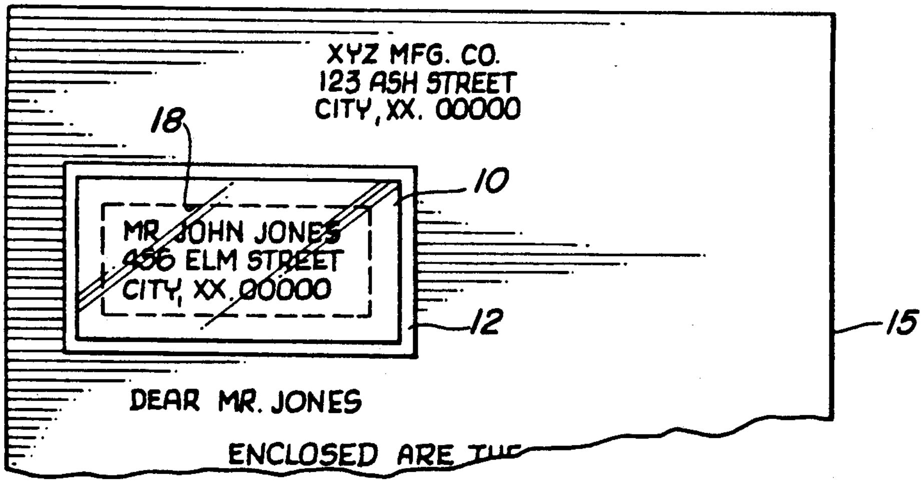
FIG. 5 is a plan view of the label of FIGS. 1 and 2 in place over an address on a donor sheet
Figure 6:
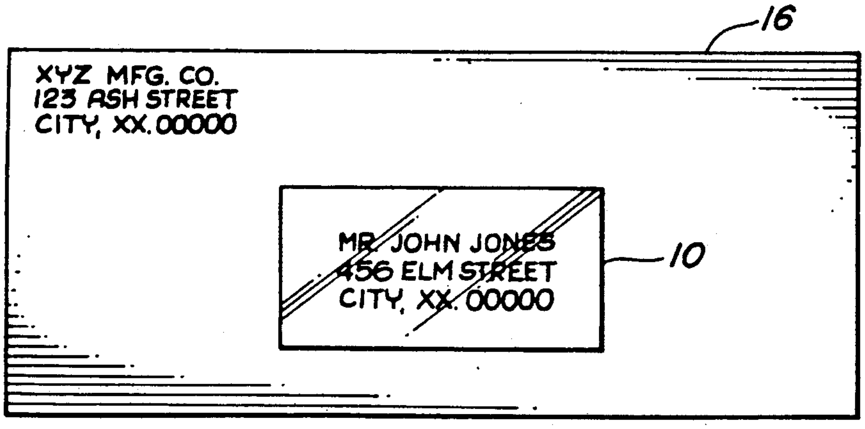
FIG. 6 is a plan view of an envelope after an address has been transferred to the envelope according to the present invention.

A third embodiment of the invention is illustrated in FIG. 4. Again, like reference numbers refer to elements having the same function. In the embodiment of FIG. 4, the microcapsules are applied to the back surface of the donor sheet instead of the face as in the previously described embodiments. The microcapsules 13 in this embodiment are held in place on a sheet 25 by a layer 24 of adhesive. The adhesive 24 should be of the removable type so that the sheet 25 can be removed from the donor sheet without damage to the donor. The sheet 25 is applied to the back of the donor sheet directly behind the image to be transferred. Since the microcapsules are not carried by label 10 in this embodiment, it is not necessary to coat the entire surface of the label with adhesive, only a peripheral band of adhesive 23 need be applied.

Rubbing the outer surface of either label 10 or sheet 25 will break the microcapsules and the contained solvent will then wet the donor sheet 15 and the image 20. The inner surface of label 10, being in contact with the image (during the rubbing) will pick up some solvated toner thus transferring the image. The label 10 can then be peeled off and affixed to its destination surface by means of adhesive 23.

As described above there is no means disclosed for holding the label assembly in position over the image on the donor sheet while the image transfer is taking place. With some care, no such means is necessary. However, it may be desirable to provide holding means as a convenience. This can be done by, for example, by coating the bottom surface of release liner 12 with a removable type of adhesive. This adhesive will function to hold the label assembly in place while the image is being transferred. In this case, release liner 14 may be made large enough to cover release liner 12 and not merely the area interior of opening 18. The removable adhesive on release liner 12 can thus be protected prior to use. Release liner 14 is removed just prior to use.

What has been described is a novel means and method for reproducing a fused toner image which have particular use in the addressing of envelopes where the letter to be mailed has been produced by a laser printer. Various modifications of the means and method as described above will no doubt occur to those skilled in the art Such modifications are intended to be covered by the following claims.

I claim:

1. An image transfer label for reproducing a xerographic image which comprises:
- a transparent substrate for receiving a transferred image;
- a layer of solvent filled microcapsules covering at least a portion of one side of said transparent substrate, said solvent being a solvent for fused xerographic toner, said microcapsules being adhered to said substrate by an adhesive; and
- means for attaching said transparent substrate to a destination surface.

2. An image transfer label as recited in claim 1 where said means for attaching said transparent substrate to a destination surface is an adhesive layer on said transparent substrate in an area outside the area covered by said microcapsules.

3. An image transfer label as recited in claim 2 and further including release liners covering said means for attaching said transparent substrate to a destination surface and said microcapsules whereby said attaching means and said microcapsules can be selectively exposed.

4. An image transfer label as recited in claim 2 where said adhesive adhering said microcapsules to said transparent substrate is different in composition or thickness with respect to said adhesive for attaching said transparent substrate to said destination surface.

5. An image transfer label as recited in claim 1 where said microcapsules are between about 80 and about 500 microns in diameter.

6. An image transfer label as recited in claim 1 where said microcapsules contain 1,1,1 trichloroethane.

7. An image transfer label as recited in claim 6 where the shells of said microcapsules ar cellulose based.

8. An image transfer label as recited in claim 1 where the shells of said microcapsules are cellulose based.

9. An image transfer label for reproducing a xerographic image which comprises:
- a transparent substrate;
- a layer of solvent filled microcapsules covering at least a portion of one side of said transparent substrate, said solvent being a solvent for fused xerographic toner, said microcapsules being adhered to said substrate by an adhesive;
- a porous sheet for receiving a transferred image covering said microcapsules;and
- means for attaching said porous sheet to a destination surface.

10. An image transfer label as recited in claim 9 where said porous sheet is a transparent porous plastic film.

11. An image transfer label as recited in claim 9 where said porous sheet is a thin paper sheet.

12. An image transfer label as recited in claim 9 where said means for attaching said transparent substrate to a destination surface is an adhesive layer on said transparent substrate in an area outside the area covered by said microcapsules.

13. An image transfer label as recited in claim 9 and further including release liners covering said means for attaching said transparent substrate to a destination surface and said microcapsules whereby said attaching means and said microcapsules ca be selectively exposed.

14. An image transfer label as recited in claim 9 where said microcapsules are between about 80 and about 500 microns in diameter.

15. An image transfer label as recited in claim 9 where said microcapsules contain 1,1,1 trichloroethane.

16. An image transfer label as recited in claim 15 where the shells of said microcapsules are cellulose based.

17. An image transfer label as recited in claim 9 where the shells of said microcapsules ar cellulose based.

18. An image transfer label for reproducing a xerographic image which comprises:
- a transparent substrate for receiving a transferred image;
- a backing sheet;
- a layer of solvent filled microcapsules covering at least a portion of one side of said backing sheet, said solvent being a solvent for fused xerographic toner, said microcapsules being adhered to said backing sheet by an adhesive;and
- means for attaching said transparent substrate to a destination surface.

19. An image transfer label as recited in claim 18 and further including means for attaching said backing sheet to the back of a page containing an image to be transferred.

20. An image transfer label as recited in claim 19 where said means for attaching said backing sheet to said page containing an image to be transferred is a layer of adhesive on said backing sheet.

21. An image transfer label as recited in claim 19 where said means for attaching said transparent substrate to a destination surface is an adhesive layer on said transparent substrate in an area outside the area covered by said microcapsules.

22. An image transfer label as recited in claim 19 and further including release liners covering said means for attaching said transparent substrate to a destination surface and said microcapsules whereby said attaching means and said microcapsules can be selectively exposed.

23. An image transfer label as recited in claim 19 where said microcapsules are between about 80 and about 500 microns in diameter.

24. An image transfer label as recited in claim 19 where said microcapsules contain 1,1,1 trichloroethane.

25. An image transfer label as recited in claim 24 where the shells of said microcapsules are cellulose based.

26. An image transfer label for reproducing an image which comprises:

a transparent substrate for receiving a transferred image;

a layer of solvent-filled microcapsules covering at least a portion of one side of said transparent substrate; and means for attaching said transparent substrate to a destination surface.

27. An image transfer label as recited in claim 26 where said means for attaching said transparent substrate to a destination surface is an adhesive layer on said transparent substrate in an area outside the area covered by said microcapsules.

28. An image transfer label as recited in claim 27 and further including a release liner covering said means for attaching said transparent substrate to a destination surface.

29. An image transfer label as recited in claim 27 and further including release liners covering said means for attaching said transparent substrate to a destination surface and said microcapsules whereby said attaching means and said microcapsules can be selectively exposed.

30. An image transfer label for reproducing an image which comprises:

a transparent substrate;

a layer of solvent filled microcapsules covering at least a portion of one side of said transparent substrate;

a porous sheet for receiving a transferred image covering said microcapsules; and means for attaching said porous sheet to a destination surface.

31. An image transfer label as recited in claim 30 where said porous sheet is a transparent porous plastic film.

32. An image transfer label as recited in claim 30 where said porous sheet is a thin paper sheet.

33. An image transfer label as recited in claim 30 where said means for attaching said porous sheet to a destination surface is an adhesive layer on at least a portion of said porous sheet.

34. An image transfer label as recited in claim 33 and further including release liner means covering said porous sheet whereby areas of said porous sheet can be selectively exposed.

35. An image transfer label for reproducing an image formed on a page which comprises:

a transparent substrate for receiving a transferred image;

a backing sheet;

a layer of solvent filled microcapsules covering at least a portion of one side of said backing sheet, and means for attaching said transparent substrate to a destination surface.

36. An image transfer label as recited in claim 35 and further including means for attaching said backing sheet to the back of said page containing an image to be reproduced.

37. An image transfer label as recited in claim 36 where said means for attaching said backing sheet to said page containing an image to be reproduced is a layer of adhesive on said backing sheet.

38. An image transfer label as recited in claim 36 where said means for attaching said transparent substrate to a destination surface is an adhesive layer on said transparent substrate.

39. An image transfer label as recited in claim 38 and further including a release liner covering said means for attaching said transparent substrate to a destination surface.

* * * * *